(12) United States Patent
Abidin et al.

(10) Patent No.: US 7,036,660 B1
(45) Date of Patent: May 2, 2006

(54) SURGICAL BLADE PACKAGE

(75) Inventors: Michael R. Abidin, 3712 Pleasant Ridge Rd., Annandale, VA (US) 22003; Steven P. Lehmbeck, 8 Roxburgh Ct., Baltimore, MD (US) 21236; Paul Varga, Chance, MD (US)

(73) Assignees: Michael R. Abidin, Annandale, VA (US); Steven P. Lehmbeck, Baltimore, MD (US); Leonard Bloom, Towson, MD (US), part interest ( * ) Notice: Subject to any disclaimer, the term of this patent is extended or adjusted under 35 U.S.C. 154(b) by 0 days.

(21) Appl. No.: 10/999,133

(22) Filed: Nov. 29, 2004

(51) Int. Cl.
  *B65D 85/00* (2006.01)
  *A45C 11/26* (2006.01)
(52) U.S. Cl. ..................... 206/354; 206/352
(58) Field of Classification Search .... 206/352 X–360, 206/354 X, 363–365, 438, 439
See application file for complete search history.

(56) References Cited

U.S. PATENT DOCUMENTS

| | | | |
|---|---|---|---|
| 4,344,532 A * | 8/1982 | Eldridge et al. | 206/370 |
| 4,395,807 A * | 8/1983 | Eldridge et al. | 29/239 |
| 4,903,390 A * | 2/1990 | Vidal et al. | 29/239 |
| 5,088,173 A * | 2/1992 | Kromer et al. | 29/239 |
| 5,250,063 A | 10/1993 | Abidin et al. | 606/167 |
| 5,275,606 A | 1/1994 | Abidin et al. | 606/167 |
| 5,411,512 A | 5/1995 | Abidin et al. | 606/167 |
| 5,433,321 A | 7/1995 | Abidin et al. | 206/354 |
| 5,496,340 A | 3/1996 | Abidin et al. | 606/167 |
| 5,528,811 A | 6/1996 | Abidin et al. | 29/428 |
| 5,569,291 A | 10/1996 | Privitera et al. | 606/185 |
| 5,662,221 A | 9/1997 | Abidin et al. | 206/354 |
| 5,662,669 A | 9/1997 | Abidin et al. | 606/167 |
| 5,699,908 A * | 12/1997 | Frye et al. | 206/355 |

* cited by examiner

*Primary Examiner*—Jila M. Mohandesi
(74) *Attorney, Agent, or Firm*—Armstrong, Kratz, Quintos, Hanson & Brooks, LLP

(57) ABSTRACT

A surgical blade package facilitates the mounting of a surgical blade on to the forwardly-projecting cleat on a scalpel handle; and following use in the O.R., the surgical blade package facilitates stripping the used blade off the scalpel for disposal in a sharps container. The cleat is inserted beneath the rear end portion of the blade, and between the blade and the bottom wall of the blade package; and forward and upward movement of the scalpel snaps the blade on to the scalpel in a continuous movement. The opposite procedure is used to demount the used blade from the scalpel and encase it in the original blade package for disposal in a sharps container.

7 Claims, 7 Drawing Sheets

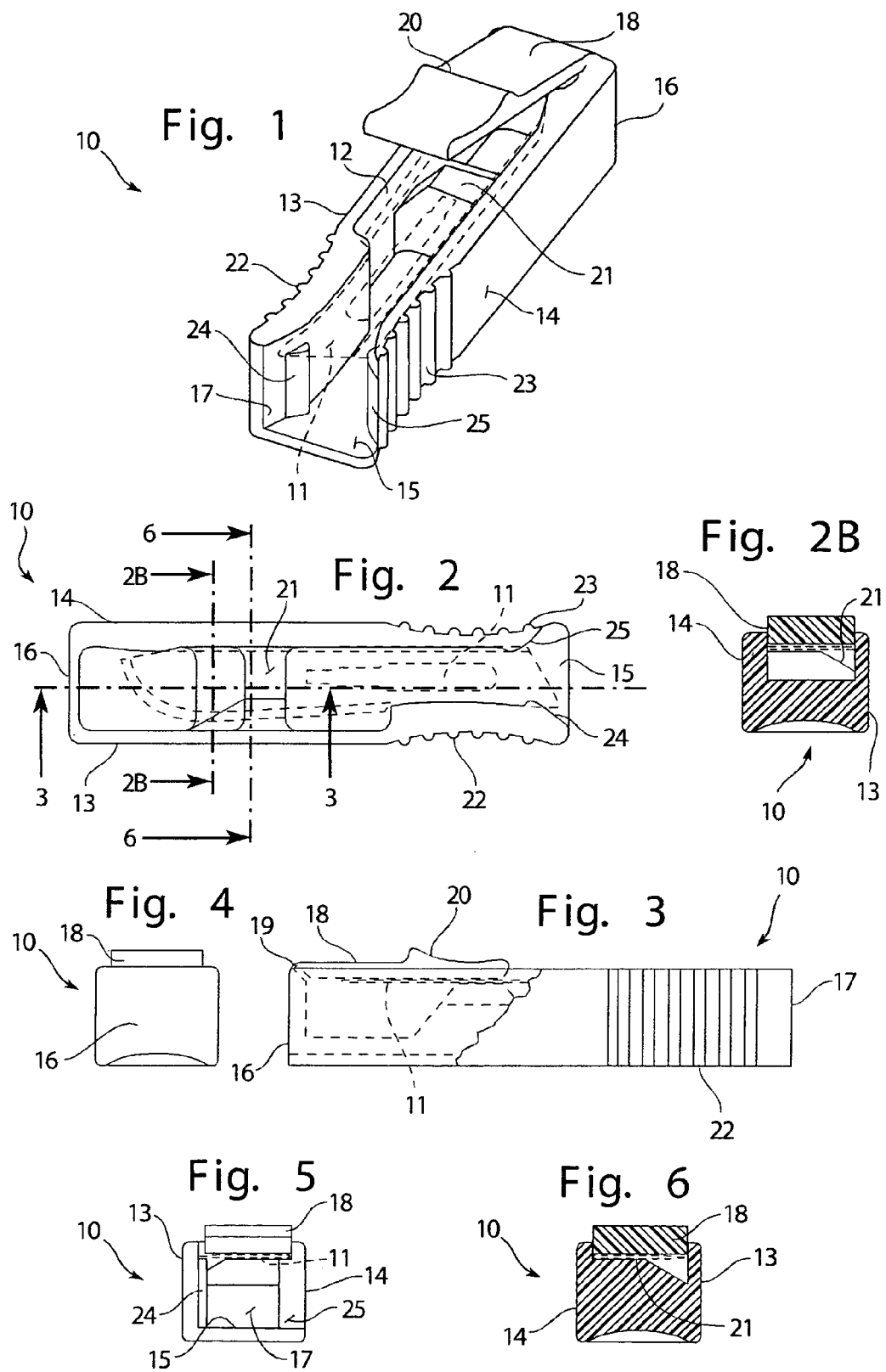

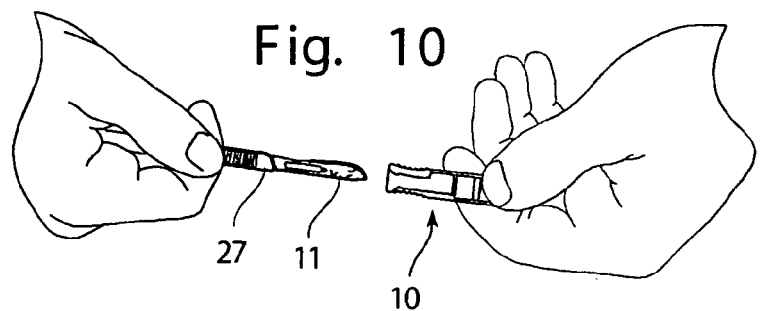
Fig. 10
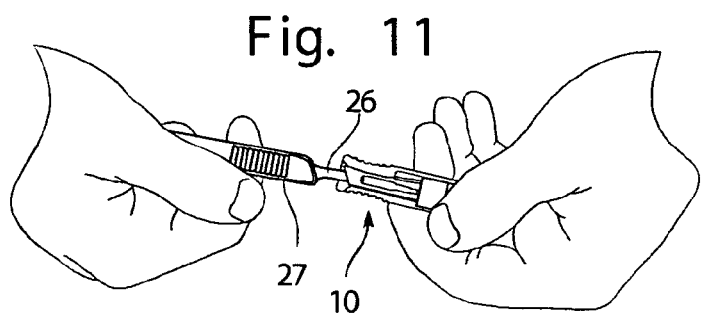
Fig. 11
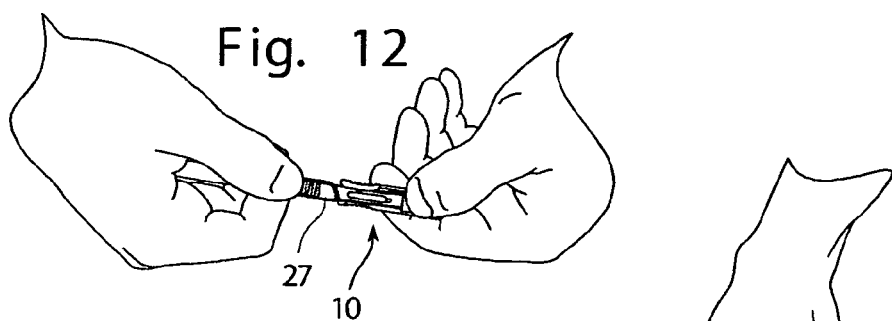
Fig. 12
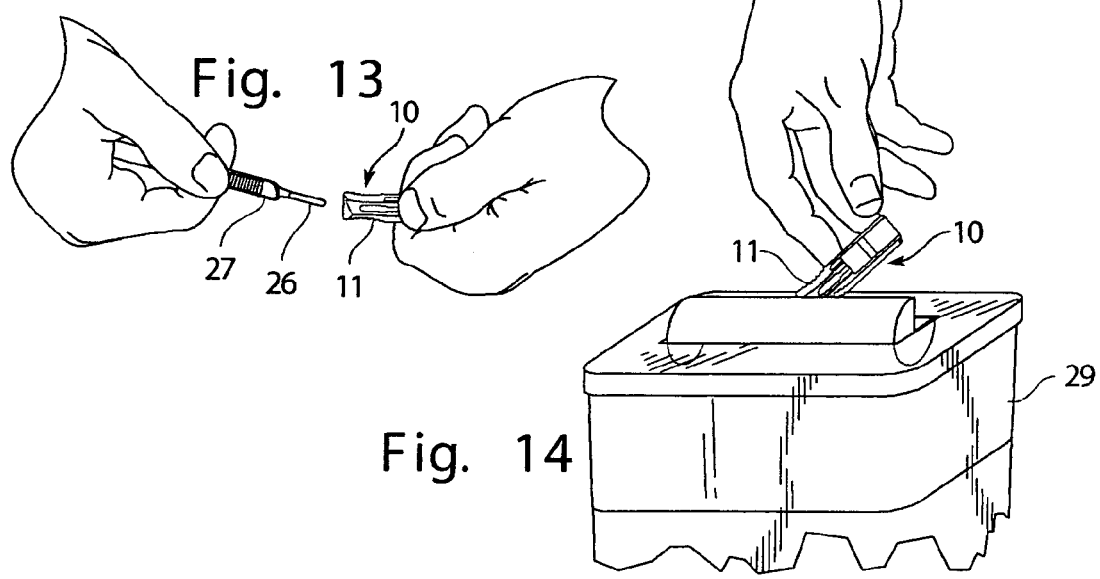
Fig. 13
Fig. 14

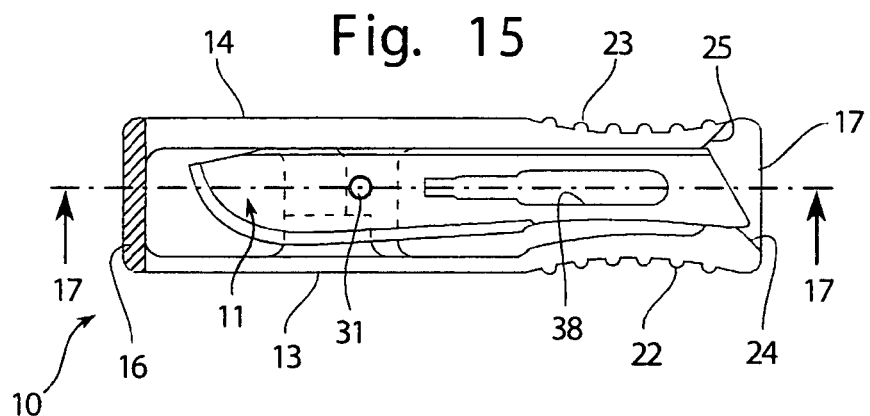
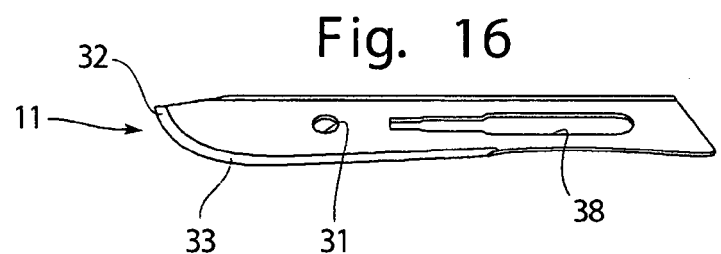
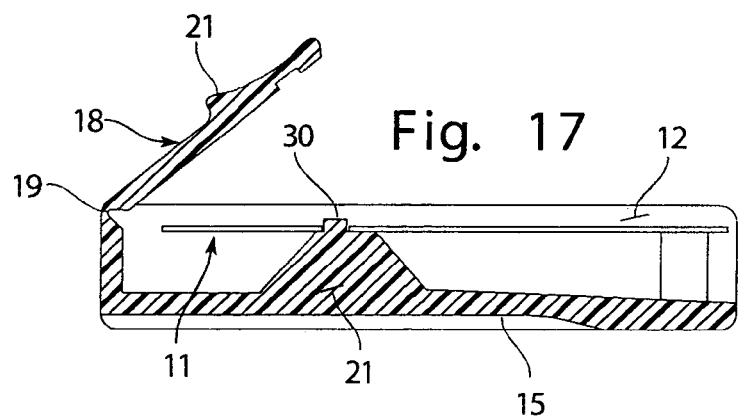
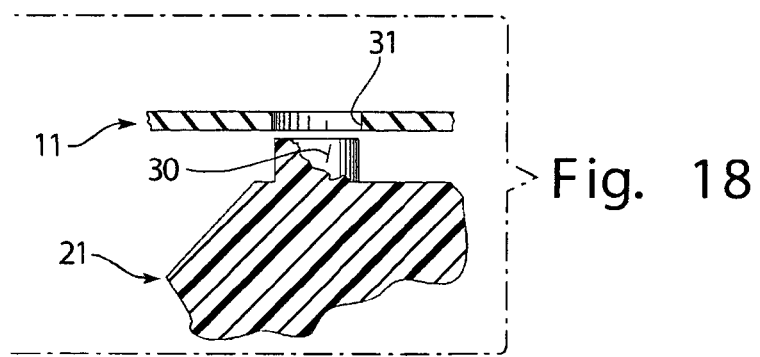

SURGICAL BLADE PACKAGE

FIELD OF THE INVENTION

The present invention relates to a surgical blade package for safely mounting a surgical blade on a scalpel handle, thereby avoiding accidental or inadvertent cuts.

BACKGROUND OF THE INVENTION

In our prior inventions, as disclosed and claimed in our United States Letters Patents—
  5,433,321
  5,528,811
  5,662,221
—a blade package is disclosed and claimed, comprising a molded-plastic closed "box", wherein the blade is retained by a pivoted flap, and wherein the forwardly-projecting cleat on the scalpel handle is inserted downwardly and forwardly into the exposed mounting slot in the blade to removably secure the blade on the cleat as the flap is pivoted away to completely disengage the scalpel from the package.

While these earlier patents are fully operational and satisfactory for the purposes intended, the present invention is the culmination of further developments and constitutes a substantial improvement thereon.

SUMMARY OF THE INVENTION

The present invention provides a surgical blade package for more easily and conveniently mounting a surgical blade on the forwardly-projecting cleat of a scalpel, thereby substantially minimizing the risk of injury by an accidental or inadvertent contact with the blade. The blade has a tip and further has a mounting slot formed therein. The surgical blade package includes a molded-plastic package having an open top and sidewalls, a bottom wall, a closed end wall and an open end oppositely of the closed end wall, respectively. A transverse ledge is disposed between the side walls, such that the blade is supported on the ledge between the side walls; the blade is substantially parallel to the bottom of the package; the tip of the blade is pointed in the direction of the closed end wall of the package; and the blade has a rear portion in juxtaposition to the open end of the package. A hold-down pivotable tab is integrally connected to the closed end wall by a living hinge. This tab partially covers the open top for retaining the blade within the package.

An important feature of the present invention is this: The cleat of the scalpel is inserted through the open rear end of the package beneath the rear portion of the blade and between the blade and the bottom wall of the package; the cleat on the scalpel is inserted into the slot in the blade; and the tab is pivoted upwardly away from the package as the blade is separated completely from the package.

In a preferred embodiment, the side walls are substantially parallel and have concavely-formed indented ("scalloped") portions adjacent to the open end of the package, such that the package may be conveniently grasped between the thumb and forefinger of one of the hands of the nurse or technician while his or her other hand is holding the scalpel, thereby providing additional leverage in separating the package from the blade on the scalpel.

In another embodiment, the package has an upstanding stud on the bottom wall thereof; and the blade has a hole formed therein to receive the stud, thereby positioning the blade laterally of the side walls of the package.

Preferably, one of the side walls of the package terminates short of the open end of the package, thereby conforming to a slanted raised portion of the conventional scalpel handle rearwardly of the cleat thereon.

Another important feature of the present invention is this: The blade may be subsequently removed from the scalpel following use of the blade during a surgical procedure in an operating room or other medical environment by reinserting the scalpel with the blade thereon into the original package, thereby stripping the blade from the cleat on the scalpel; and the tab is pressed down on the blade to retain the blade, such that the package with the used blade therein may be placed into a sharps container.

Preferably, cooperating nibs are formed between the pivotable tab and the package, thereby releasably holding the tab down on the blade, such that the cooperating nibs are released as the cleat on the scalpel is mounted into the slot in the blade and the scalpel is moved away from the package.

A sealed, sterile, pouch may be provided for the blade package.

Viewed in another aspect, the present invention provides, in combination, a surgical blade package and a surgical blade contained therein, the blade having a slot formed therein for receiving a forwardly projecting cleat on a scalpel as the scalpel is inserted into the package. Following use of the blade in an operating room or other medical or surgical environment, the blade may be stripped of the scalpel by reinserting the cleat into the package, thereby eliminating or at least substantially minimizing the risk of injury by an accidental or inadvertent contact with the blade. Means are provided for supporting the blade within the package and for preventing an inadvertent dulling of the blade during manufacture, shipment or storage thereof, and releasable means are provided on the package for holding and retaining the blade prior to insertion of the scalpel into the package. The scalpel is inserted beneath the rear portion of the blade and between the blade and a bottom wall of the package, and the scalpel is moved forwardly and upwardly (not downwardly as in our previous patents) relative to the package to mount the blade on the scalpel as the blade is completely removed from the package. After a surgical procedure, the blade is re-inserted within the package and the relative movement of the scalpel and package is reversed to strip the blade off the scalpel; thereafter, the nurse or technician uses the releasable means to again retain the blade prior to disposal of the package with the blade into a sharps container or other disposable means.

Preferably, the means for supporting the blade within the package comprises a transverse ledge formed on the package. In one embodiment, this ledge is formed between parallel side walls of the package and intermediately of the length of the package.

The releasable means for holding down and retaining the blade comprises a tab integrally connected to the package by a living hinge.

Viewed in yet another aspect, the present invention provides a method of more easily and conveniently mounting a surgical blade on the forwardly-projecting cleat of a scalpel, and for subsequently removing the blade from the scalpel following use of the blade during a surgical procedure in an operating room or other medical environment, thereby eliminating or at least substantially minimizing the risk of injury due to an accidental or inadvertent contact with the blade. This improved method includes the steps of provides a package having a blade therein, the blade being disposed between respective side portions of the package and further being recessed below the open top the package. A tab is formed on the package and partially covers the open top of the package above the blade. The package is held with one hand while holding the scalpel with the other hand. The cleat on the scalpel is inserted underneath the rear portion of the blade and between the blade and the package. The scalpel is moved forwardly and upwardly with respect to the package such that the cleat on the scalpel is received within the slot on the blade, and such that diametrically-opposite slits on the cleat engage the respective adjacent sides of the slot in the blade. The forward movement of the scalpel is continued, such that the tab on the package is pushed away as the package is separated from the blade and the blade is mounted on the scalpel.

Following use of the scalpel with the blade mounted thereon during a surgical procedure, the improved method includes the steps of picking up the package; maintaining the flap down on the package; reinserting the blade into the package to completely strip the blade away from the package; and thereafter disposing of the package with the blade therein in a suitable container.

In accordance with the teachings of the present invention, the improved surgical blade package may be used with a standard (unguarded) scalpel handle or with a guarded surgical scalpel as disclosed and claimed in our following United States Letters Patents:

5,250,063
5,275,606
5,411,512
5,496,340
5,569,291
5,662,669

These and other objects of the present invention will become apparent from a reading of the following specification, taken in conjunction with the enclosed drawings.

BRIEF DESCRIPTION OF THE DRAWINGS

FIG. 1 is a perspective view of the improved surgical blade package of the present invention.

FIG. 2 is a top plan view thereof, the broken lines indicating the blade.

FIG. 3 is a longitudinal section view, taken along the lines 3—3 of FIG. 2, and with certain parts shown in elevation and section, respectively.

FIG. 4 is a forward end view (the closed end) of the blade package of FIG. 1.

FIG. 5 is the rear opposite end view (the open end) of the package.

FIG. 6 is a cross-sectional view, taken along the lines 6—6 of FIG. 2, and showing the blade between the pivoted tab (or flap) and the transverse ledge for supporting the blade thereon.

In FIGS. 7A and 8A, the scalpel handle is held in one hand and the blade package in the other hand.

In FIGS. 7B and 8B, the forwardly-projecting cleat on the scalpel is inserted through the open end of the package, beneath the blade, and between the blade and the bottom wall of the package.

In FIGS. 7C and 8C, the cleat on the scalpel is fully inserted into the mounting slot on the blade, as the cleat is moved forwardly and upwardly relative to the package.

In FIGS. 7D and 8D, the forward, upward movement of the scalpel is continued (it's all one continuous movement to "snap" the blade on the scalpel) and, as shown, the package is completely disengaged from the scalpel.

FIGS. 10–14 illustrate the sequential steps of the stripping the used blade off the scalpel, using the original blade package (and substantially reversing the steps in snapping or inserting the blade on the scalpel) for subsequent disposal of the package (with the used blade therein) in a suitable "sharps" container (FIG. 14).

FIGS. 15–18 illustrate a further embodiment, wherein an upwardly-projecting integrally-molded stud cooperates with a hole in the blade for precluding lateral movement of the blade in the package during manufacture, shipment and/or storage, thereby precluding inadvertent dulling of the blade.

FIG. 15 is a top plan view of this further embodiment of the blade and its package.

FIG. 16 is a top plan view of the blade of FIG. 15.

FIG. 17 is a longitudinal section, taken along the lines 17—17 of FIG. 15 and showing the pivoted tab lifted away from the blade.

FIG. 18, drawing to an enlarged scale, illustrates the cooperation of the upstanding pin or stud and the hole (or other opening) in the blade.

FIG. 19 is a partial top plan view thereof, drawn to an enlarged scale.

FIG. 20 is a fill top plan view thereof.

FIG. 21 is a cross-sectional view thereof, taken along the lines 21—21 of FIG. 20, and drawn to an enlarged scale.

FIG. 22 is a longitudinal section view thereof, taken along the lines 22—22 of FIG. 20, and showing alternate positions of the pivoted tab in broken lines.

GENERAL DESCRIPTION OF THE PREFERRED EMBODIMENTS

Figure 7A:
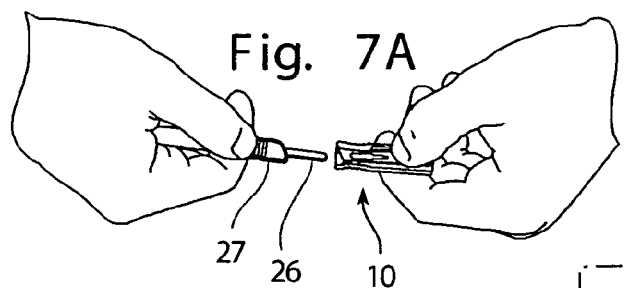
FIGS. 7A–7D and 8A–8D are respective sequence views, illustrating the mounting of the blade on the scalpel.
Figure 8A:
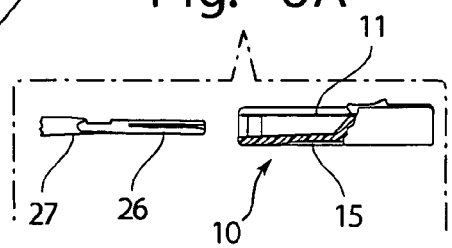
Figure 7B:
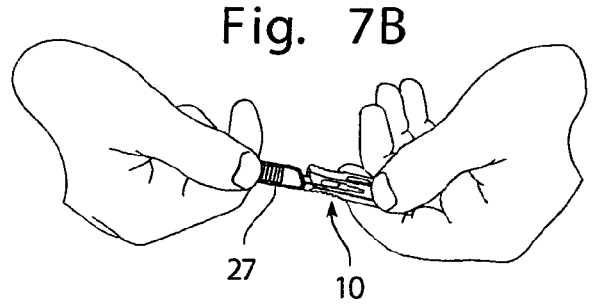
Figure 8B:
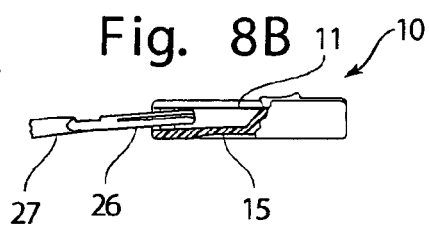
Figure 7C:
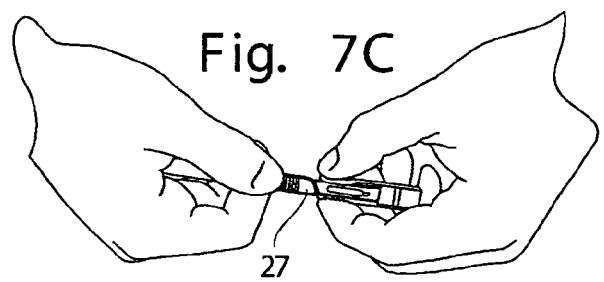
Figure 8C:
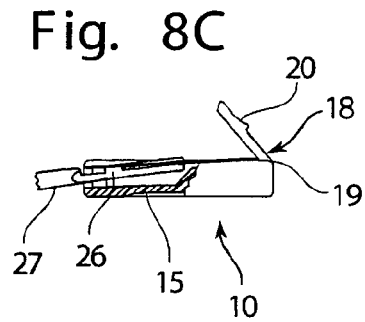
Figure 7D:
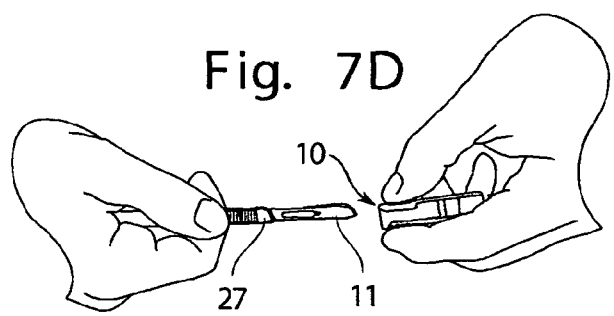
Figure 8D:
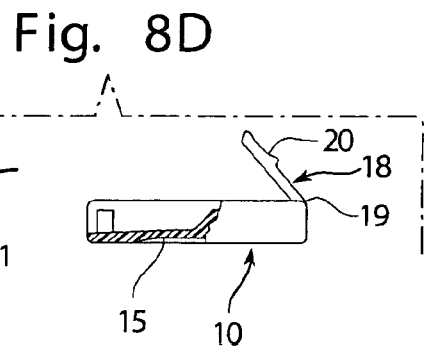
Figure 9:
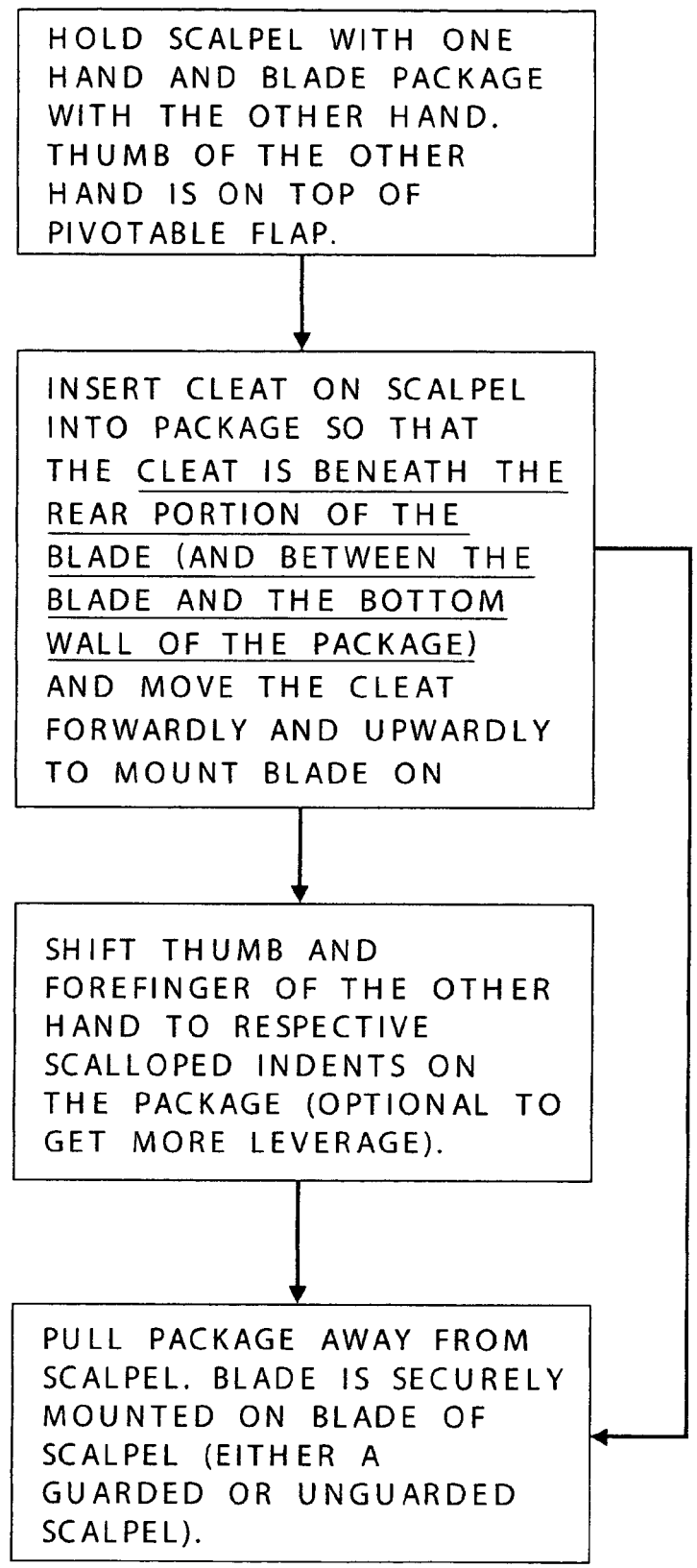
FIG. 9 is a flow chart, showing the sequential steps in mounting the blade on the scalpel and disengaging the blade package (which is saved for subsequent disposal of the used blade).
Figure 19:
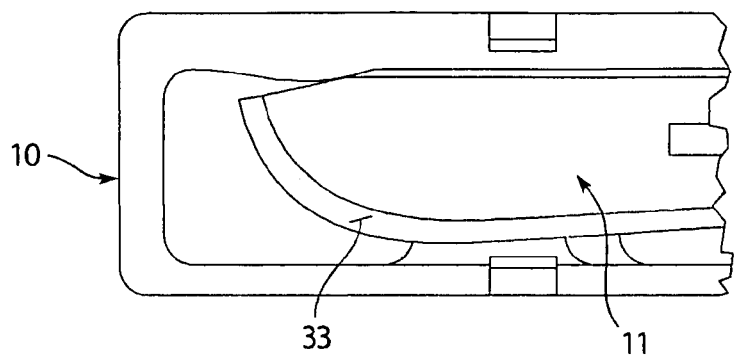
FIGS. 19–22 show a still further embodiment, wherein cooperating nibs are formed between the pivoted tab and the side walls of the blade package for a stronger cooperation therebetween.
Figure 20:
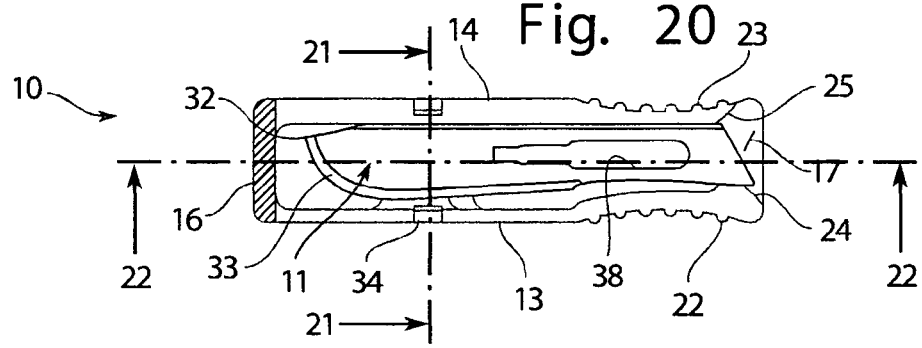
Figure 21:
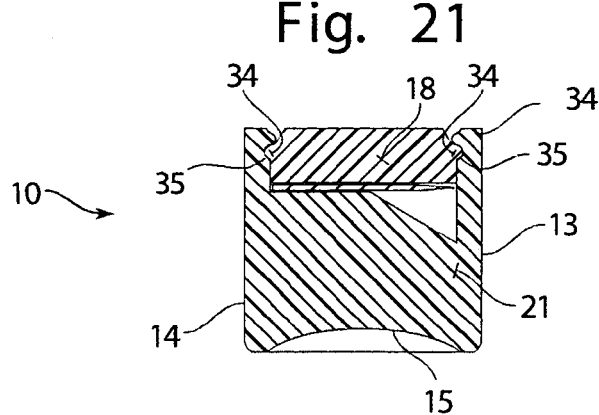

With reference to FIGS. 1–6, the improved blade package 10 houses a surgical blade 11. The package 10 has an open top 12, side walls 13 and 14, a bottom wall 15, a closed forward end 16 and an open rear end 17. A pivotable tab (or flap) 18 partially covers the open top 12 and is joined to the package 10 by an integrally-molded "living" hinge 19. The tab 18 has a raised thumb rest 20. The blade 11 is supported upon a transverse ledge 21 joining the respective side walls 13 and 14 intermediately the length of the blade package 10. The side walls 13 and 14 have indented or scalloped recesses 22 and 23, respectively, adjacent to the open rear end 17 of the package 10 and, preferably, these recesses 22 and 23 are suitable grooved (or knurled or roughened) as shown for holding the blade package 10 between the thumb and forefinger. The open rear end 17 of the package 10 (see FIG. 1) has guides 24 and 25, respectively, for slidably guiding the scalpel into the blade package 10 (as hereinafter described).

With reference to FIGS. 7A–7D, 8A–8D and 9, the forwardly-projecting cleat 26 on the conventional scalpel handle 27 is inserted beneath the rear end portion 28 of the blade 11 and between the blade 11 and the bottom wall 15 of the package 10 (FIGS. 7B and 8B) and the cleat 26 is continued upwardly and forwardly (FIGS. 7C and 8C) until the blade 11 snaps on to the cleat 26 on the scalpel 27 and the blade package 10 is disengaged from the scalpel 27 (FIGS. 7D and 8D) in one continuous upward and forward movement.

With reference again to FIG. 9, the blade package 10 may be pulled away from the scalpel 27 (all in one motion) or, if desired, the operator's thumb and forefinger may be shifted into the scalloped concave recesses 22 and 23, respectively, to assure a better manual grip and obtain more leverage.

Once the blade 11 has been used in a surgical procedure, the reverse steps may be employed to re-position the (used) blade 11 in the original package 10 for disposal purposes.

This reverse procedure is shown in FIGS. 10–14, respectively. Again, the scalpel 27 (with the used blade 11 thereon) is held in one hand (FIG. 10) and the blade 11 is inserted into the package 10 (FIG. 11) and continued therein (FIG. 12) to strip the blade 11 off the scalpel 27, whereupon the blade 11 is wholly within the package 10 and completely removed from the scalpel 27 (FIG. 13) so that the package 10 (with the used blade 11 therein) may be tossed into a conventional "sharps" container 29.

With reference to FIGS. 15–18, a modification is illustrated wherein the transverse ledge 21 on the blade package 10 has an upstanding pin or stud 30 (or other projection) received in a hole 31 (or other opening) formed in the blade 11. The cooperation therebetween provides additional assurance that the blade 11 will not shift laterally during manufacture, shipment and/or storage of the blade package 10, thereby assuring that the tip 32 and cutting edge 33 of the blade 11 will not become dulled or nicked.

Figure 22:
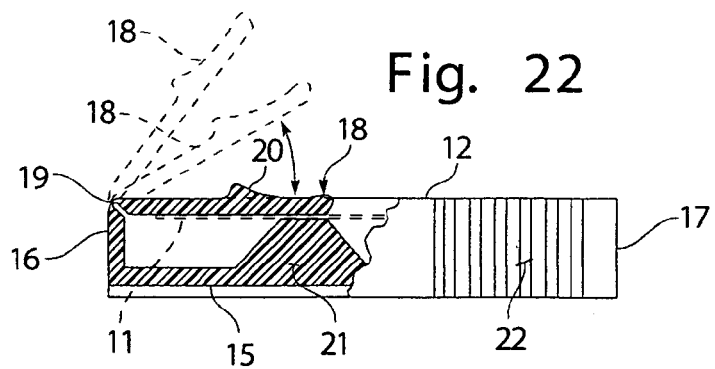

With reference to FIGS. 19–22, a second modification is illustrated wherein the pivotable tab 18 has a pair of oppositely-disposed projections or nibs 34 (FIG. 21) received in cooperating recesses 35 in the sidewalls 13 and 14, respectively, of the blade package 10, thereby more securely retaining the pivotable tab 18 against accidental or inadvertent dislodgement from the open top 12 of the blade package 10. The retaining force of these nibs 34, however, will not interfere with the upwardly and forwardly movement of the scalpel 27 to mount the blade 11 on to the cleat 26 of the scalpel 27 and, using the inherent mechanical advance, pivot the tab 18 away from the open top 12 of the blade package 10 (FIG. 22).

Figure 23:
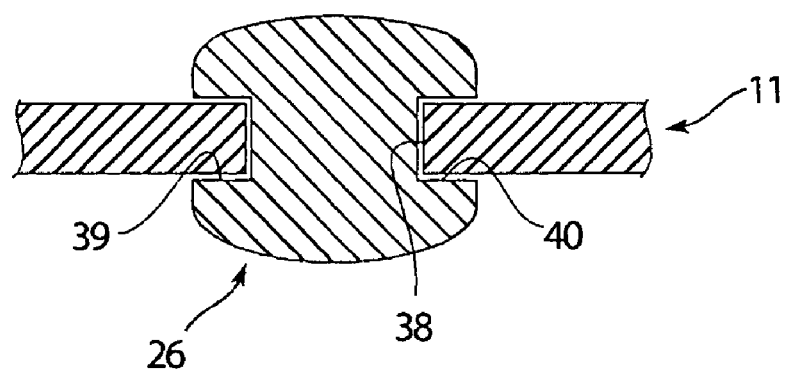
FIG. 23 is a cross-sectional view, drawn to an enlarged scale, showing the cleat on the scalpel received in the mounting slot in the blade, the side edges of the blade (adjacent to the mounting slot in the blade) being recessed within the diametrically-opposite slits in the cleat on the scalpel handle.

With reference to FIG. 23, and as is conventional, the side edges 36 and 37, respectively, of the blade 11 (adjacent to the mounting slot 38 are received in the slits 39 and 40, respectively, of the cleat 26 on the scalpel 27.

Figure 24:
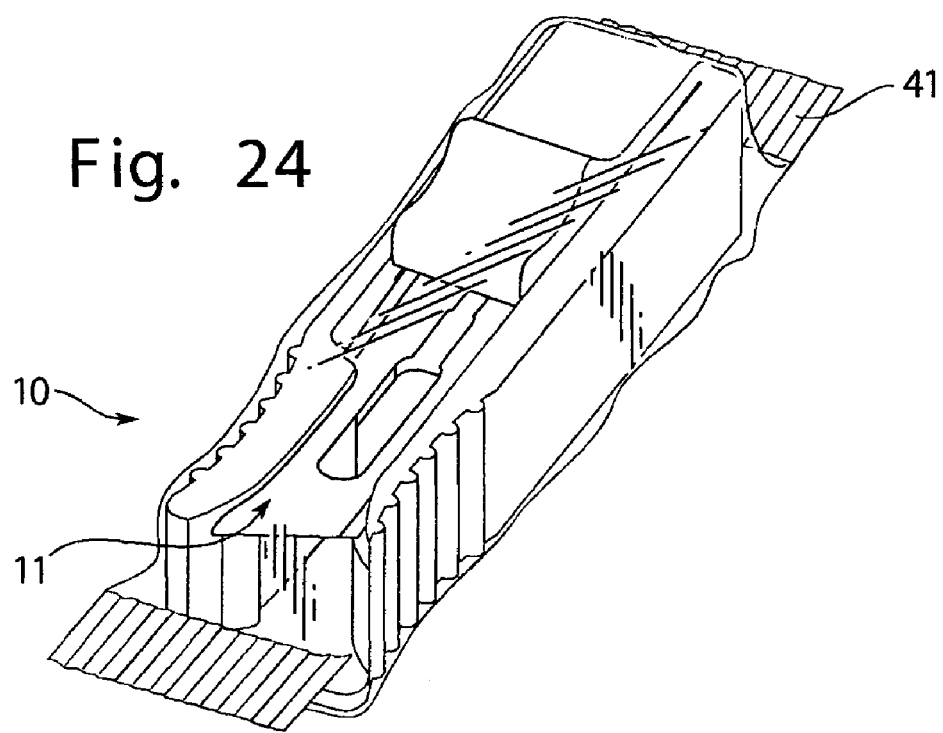
FIG. 24 is a perspective view of the blade package of the present invention (with the surgical blade therein) recessed within a sterile pouch (or other sterile container).

With reference to FIG. 24, the blade package 10 may be received in a suitable pouch 41 (which is sterilized). In lieu of the pouch 41, a blister pack, foil or other suitable container (not shown) may be employed for the blade package 10.

As will be appreciated by those skilled in the art, the blade package 10 of the present invention is a decided improvement over the prior art (including our own patents) and constitutes an important and valuable contribution in the art. Not only is the operation different and superior (an upward movement rather than a downward movement) but, even more significantly, the original blade package 10 becomes the disposable package or container for the used blade 11.

Obviously, many modifications may be made without departing from the basic spirit of the present invention. Accordingly, it will be appreciated by those skilled in the art that within the scope of the appended claims, the invention may be practiced other than has been specifically described therein.

What is claimed is:

1. A surgical blade package for easily and conveniently mounting a surgical blade on the forwardly-projecting cleat of a scalpel, thereby substantially minimizing the risk of injury by an accidental or inadvertent contact with the blade, the blade having a tip and further having a mounting slot formed therein, the surgical blade package comprising a molded-plastic package having an open top and sidewalls, a bottom wall, a closed forward end wall and an open rear end oppositely of the closed forward end wall, respectively, a raised transverse ledge between the side walls, such that the blade is supported on the ledge between the side walls, wherein the blade is substantially horizontal and parallel to the bottom wall of the package, the tip of the blade is pointed in the direction of the closed end wall of the package, and the blade having a rear portion in juxtaposition to the open rear end of the package; a pair of spaced-apart vertical guides at the open rear end of the package; and a hold-down pivotable tab integrally connected to the closed end wall by a living hinge, the tab partially covering the open top for retaining the blade within the package, the end of the pivotable tab being substantially coterminous with the raised transverse ledge, such that when the cleat of the scalpel is inserted upwardly through the open rear end of package, between the spaced-apart vertical guides, beneath the rear portion of the blade and between the blade and the bottom wall of the package, the cleat on the scalpel is inserted into the slot in the blade, and the tab is pivoted upwardly away from the package as the blade is separated completely from the package.

2. The surgical blade package of claim 1, wherein the side walls are substantially parallel, and wherein the side walls have concavely-formed indented portions adjacent to the open end of the package, such that the package may be conveniently grasped between the thumb and forefinger of one of the hands of the nurse or technician while his or her other hand is holding the scalpel, thereby providing additional leverage in separating the package from the blade on the scalpel.

3. The surgical blade package of claim 1, wherein the package has an upstanding stud on the bottom wall thereof, and wherein the blade has a hole formed therein to receive the stud, thereby positioning the blade laterally of the side walls of the package.

4. The surgical blade package of claim 1, wherein one of the side walls terminates short of the open end of the package, thereby conforming to a slanted raised portion of the scalpel rearwardly of the cleat thereon.

5. The surgical blade package of claim 1, wherein the blade may be subsequently removed from the scalpel following use of the blade during a surgical procedure in an operating room or other medical environment by reinserting the scalpel with the blade thereon into the package, thereby stripping the blade from the cleat on the scalpel, and thereafter pressing down the tab on the blade to retain the blade, such that the package with the blade therein may be placed into a sharps container.

6. The surgical blade package of claim 1, further including cooperating nibs between the pivotable tab and the package, thereby releasably holding the tab down on the blade, and such that the cooperating nibs are released as the cleat on the scalpel is mounted into the slot in the blade and the scalpel is moved away from the package.

7. The surgical blade package of claim 1, further including a sealed sterile pouch for the package.

* * * * *